(12) United States Patent
Frye et al.

(10) Patent No.: US 8,937,202 B2
(45) Date of Patent: Jan. 20, 2015

(54) PROCESSES AND SYSTEMS FOR THE PRODUCTION OF PROPYLENE GLYCOL FROM GLYCEROL

(75) Inventors: John G. Frye, Richland, WA (US); Aaron A. Oberg, Richland, WA (US); Alan H. Zacher, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 576 days.

(21) Appl. No.: 12/711,053

(22) Filed: Feb. 23, 2010

(65) Prior Publication Data

US 2011/0207971 A1 Aug. 25, 2011

(51) Int. Cl.
*C07C 31/18* (2006.01)
*C07C 31/20* (2006.01)
*C07C 29/60* (2006.01)

(52) U.S. Cl.
CPC ................................ *C07C 29/60* (2013.01)
USPC .................................. 568/861; 568/862

(58) Field of Classification Search
None
See application file for complete search history.

(56) References Cited

U.S. PATENT DOCUMENTS

| | | | |
|---|---|---|---|
| 4,716,142 A | 12/1987 | Laine et al. | |
| 6,291,725 B1 * | 9/2001 | Chopade et al. | 568/861 |
| 6,479,713 B1 | 11/2002 | Werpy et al. | |
| 6,670,300 B2 | 12/2003 | Werpy et al. | |
| 6,677,385 B2 | 1/2004 | Werpy et al. | |
| 6,706,893 B2 | 3/2004 | Werpy et al. | |
| 6,841,085 B2 | 1/2005 | Werpy et al. | |
| 6,982,328 B2 | 1/2006 | Werpy et al. | |
| 7,038,094 B2 | 5/2006 | Werpy et al. | |
| 7,186,668 B2 | 3/2007 | Werpy et al. | |
| 7,199,250 B2 | 4/2007 | Werpy et al. | |
| 7,619,118 B2 | 11/2009 | Arredondo et al. | |
| 8,252,961 B2 * | 8/2012 | Suppes | 568/861 |
| 2007/0287865 A1 | 12/2007 | Arredondo et al. | |
| 2008/0045749 A1 | 2/2008 | Arredondo et al. | |
| 2008/0103339 A1 | 5/2008 | Bloom | |
| 2008/0216391 A1 | 9/2008 | Cortright et al. | |
| 2008/0242898 A1 | 10/2008 | Miller et al. | |
| 2009/0062578 A1 | 3/2009 | Koivusalmi et al. | |
| 2009/0069610 A1 | 3/2009 | Roberts, IV et al. | |
| 2009/0105509 A1 | 4/2009 | Suppes | |
| 2010/0019192 A1 * | 1/2010 | Suppes et al. | 252/73 |
| 2010/0151535 A1 | 6/2010 | Franklin et al. | |
| 2011/0112335 A1 * | 5/2011 | Godavarthy et al. | 568/861 |

FOREIGN PATENT DOCUMENTS

| | | |
|---|---|---|
| EP | 2 070 902 A1 | 6/2009 |
| WO | WO-2009/045606 A1 | 4/2009 |
| WO | WO 2009111352 A1 * | 9/2009 |
| WO | WO 2010/002618 A1 | 1/2010 |
| WO | WO 2010/014145 A2 | 2/2010 |
| WO | WO 2010-032748 A1 | 3/2010 |
| WO | WO 2010-068904 A2 | 6/2010 |

OTHER PUBLICATIONS

PCT—International Search Report dated Jul. 26, 2011 (4 pages).
PCT—Written Opinion of the International Searching Authority dated Jul. 26, 2011 (7 pages).
U.S. Appl. No. 12/711,020, filed Feb. 23, 2010, Brown et al.
PCT—International Search Report dated Sep. 7, 2011 (4 pages).
PCT—Written Opinion of the International Searching Authority dated Sep. 7, 2011 (7 pages).
$2^{nd}$ Office Action issued in China Patent Application No. 201080066374.3, with English Translation, dated Sep. 16, 2014, 27 pages.
Jian et al., Studies and Applications of Catalytic Hydrongenolysis of Glycerol [with English Abstract], Progress in Chemistry, vol. 19, No. 5, May 2007, 8 pages.

* cited by examiner

*Primary Examiner* — Nyeemah A Grazier
(74) *Attorney, Agent, or Firm* — Klarquist Sparkman, LLP

(57) ABSTRACT

Processes and systems for converting glycerol to propylene glycol are disclosed. The glycerol feed is diluted with propylene glycol as the primary solvent, rather than water which is typically used. The diluted glycerol feed is sent to a reactor where the glycerol is converted to propylene glycol (as well as other byproducts) in the presence of a catalyst. The propylene glycol-containing product from the reactor is recycled as a solvent for the glycerol feed.

9 Claims, 1 Drawing Sheet

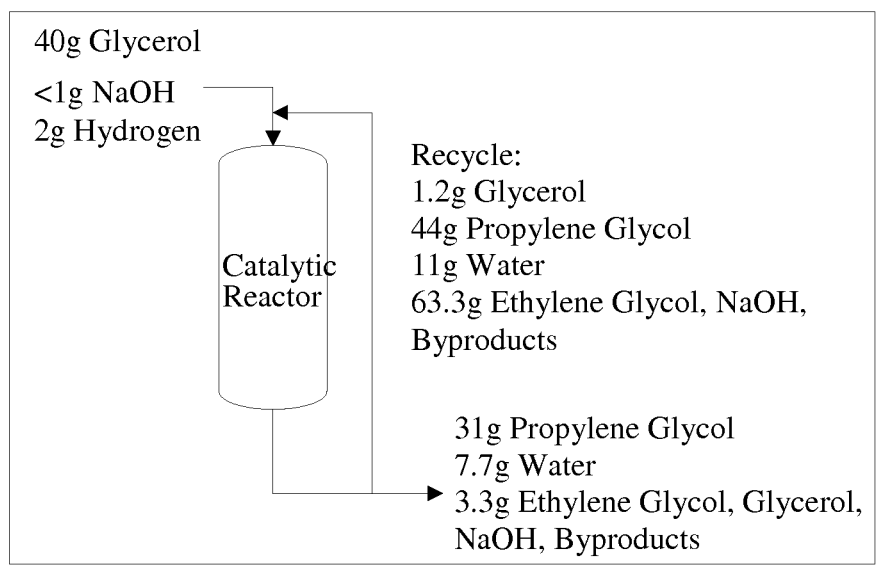

PROCESSES AND SYSTEMS FOR THE PRODUCTION OF PROPYLENE GLYCOL FROM GLYCEROL

ACKNOWLEDGMENT OF GOVERNMENT SUPPORT

This invention was made with Government support under Contract DE-AC06-76RLO1830 awarded by the U.S. Department of Energy. The Government has certain rights in the invention.

FIELD

This disclosure relates to processes and systems for the conversion of glycerol to propylene glycol, including processes that recycle the propylene glycol product stream to serve as a solvent for the glycerol feed stream.

BACKGROUND

It is known to convert glycerol to propylene glycol. Glycerol that is derived from a bio-diesel process has to be treated in a number of steps prior to its conversion to propylene glycol. For instance, one step includes the acidification of the glycerol feed to decant the free fatty acids. In addition, the glycerol is often thermally stripped to remove methanol. Thermally stripping the glycerol feed to remove methanol, however, has the adverse consequence of removing much of the water that is otherwise necessary to enable the catalytic process. Thus, concentrated glycerol feed must be diluted with water to about 40% to 60% by weight prior to its use as reactor feed. However, the necessary addition of water to the feed stream places a burden on the overall system since it must later be removed in downstream distillation separation processes. As such, having to remove water that was just added in previous steps is energy inefficient, and increases production time and the overall cost of the process.

Further, once the concentrated glycerol is diluted with water, a base reagent (such as sodium hydroxide) must be added to the glycerol before it can be used as reactor feed. Unfortunately, the base reagent that leaves with the reactor product is not easily recycled and is wasted during the recovery process. Finally, there is significant data on this process that suggests that in many cases the process operates near a hydrogen mass transport limited regime.

Accordingly, there exists a need for improved processes to convert glycerol to propylene glycol.

SUMMARY

Processes and systems for converting glycerol to propylene glycol are disclosed. The glycerol feed is diluted with propylene glycol as the primary solvent, rather than water which is typically used. The use of water as a solvent is disadvantageous since, among other things, it must later be removed by downstream separation processes. The diluted glycerol feed is sent to a reactor (such as a trickle-bed reactor) where the glycerol is converted to propylene glycol (as well as other byproducts) in the presence of a catalyst. The propylene glycol-containing product from the reactor is recycled back as a solvent for the glycerol feed. In certain embodiments, the amount of water in the recycle solvent stream is less than about 20% by weight, and the diluted glycerol feed contains less than about 12% water by weight.

Also disclosed is a system for converting glycerol to propylene glycol. The system includes a reactor containing a catalyst for facilitating the conversion of glycerol into propylene glycol. The system also includes a glycerol feed stream that has been primarily diluted with propylene glycol rather than water in order to facilitate the reaction chemistry and the catalytic conversion of the glycerol to propylene glycol. Also disclosed as part of the system is a recycle stream whereby the reaction product, or a portion of the reaction product, is fed back to dilute the glycerol feed stream.

In certain embodiments, the diluted glycerol feed comprises from about 40% to 60% by weight propylene glycol. In another aspect, the diluted glycerol feed comprises from about 40% to 60% by weight glycerol. In certain disclosed embodiments, the reaction is carried out at a temperature from about 160° C. to about 240° C., and at pressures from about 400 to about 1600 psi.

The foregoing and other objects, features, and advantages of the processes and systems disclosed herein will become more apparent from the following detailed description.

BRIEF DESCRIPTION OF THE DRAWINGS

FIG. 1 is a diagram illustrating the use of reactor effluent as the primary solvent instead of water.

DETAILED DESCRIPTION

Glycerol that has been generated from the biodiesel process is mostly free of water after the final methanol recovery step, yet its catalytic upgrading to propylene glycol requires up to 60% solvent by weight to enable the reaction chemistry. This is particularly troublesome since the water must be subsequently removed in immediate and costly downstream separations. The elimination of water as a solvent would provide a more efficient and resourceful process, and would provide cost savings on both reactor operations and separations.

As illustrated in FIG. 1, an alternate reactor configuration was proposed using reactor effluent as the primary reactor solvent instead of water. In this embodiment, an internal recycle of nearly 60% was proposed. Although the amount of the product stream proposed to be recycled is quite large, it was anticipated that this process could yield certain advantages when compared to the baseline process.

Specifically, the water load to separations would be reduced by about 90%, and overall product sent to separations would be reduced by more than half while still maintaining the same rate of propylene glycol output. The reactor size would remain nearly the same. The recycled solvent would come in near reaction temperature, thereby reducing the need for added energy requirements. The base and some glycerol are also partially recycled in the system, thereby resulting in a more resourceful and efficient process.

It was also anticipated that the process could suffer from several disadvantages. Specifically, stability of propylene glycol becomes a crucial factor and any consumption of propylene glycol would have a magnified effect on the true process yield. Also, byproduct recycle could lead to unwanted effects on the primary chemistry, and possibly produce a more recalcitrant byproduct in the separation processes. In addition, propylene glycol as a solvent could affect the catalytic chemistry, including diffusion limitations or reduced hydrogen access to the catalyst.

The disclosed embodiments address the issues that have arisen as a result of the use of biodiesel derived glycerol and the need for the addition and immediate subsequent removal of water primarily around the catalysis unit operation. In particular, disclosed are processes and systems wherein reactor product from the conversion of glycerol to propylene glycol is recycled and used as the primary solvent instead of water in order to dilute the concentrated glycerol feed stream. In known processes, the glycerol feed stream must first be diluted with water to about 40-60% by weight. The substitution of the reactor product as the feed solvent would advantageously impact the efficiency and economics of the process.

In one embodiment, the process involves diluting the concentrated glycerol to 40% to 60% by weight with unseparated process product consisting of concentrated propylene glycol, reaction product water, unreacted glycerol, minimal byproducts, and sodium hydroxide or other base. The propylene glycol from the reactor is in a concentrated form with about as low as 20% water (from dehydroxylation), thereby relieving the otherwise significant cost of removing the diluent water in a downstream separation process. Also, since the reactor does not have to be sized larger for the processes disclosed herein, separation costs would therefore be reduced. Some of the sodium hydroxide or base is recycled in the feed through the reactor product diluents. In addition, unreacted glycerol feed is also recycled in the process, thereby increasing the overall resourcefulness and efficiency of the system.

The recycling of the product stream also allows for higher solubility of hydrogen in the liquid phase during the catalytic reaction. This is a creative way of eliminating the hydrogen diffusion limitations that have bounded the process to only certain conditions, and may open up much higher reaction rates than previously allowed. In current processes using water as the diluent, hydrogen starvation of the catalyst often occurs at high reaction rates, thereby depressing selectivity and making significant amounts of byproducts.

A reactor product feed simulant was used for the proof of principle testing. The feed was composed of the products resulting from a 90% yield from glycerol but was prepared without byproduct simulants. The feed consisted of about 40% glycerol, 47% propylene glycol, 1% Base, and 12% water by weight. This is similar to the theoretical reactor feed comprised of about 41% glycerol, 44% propylene glycol, 11% water, 1% base, and 3% byproducts.

As this was a proof of principle test, it was decided to examine the reactor product feed simulant at the end of standard screening tests. Referring to Table 1, test run F167 was a screening test for 2.5% Co/0.45% Pd/2.4% Re catalyst on a carbon support. (This catalyst had a lower than normal performance when compared to the baseline catalyst system.) The system was processed at the baseline screening conditions of 190° C. with 1200 psi of hydrogen at a 5:1 molar ratio to the glycerol. The feed rate was 35 ml/hr and included approximately 40.6% by weight laboratory grade glycerol and 1% by weight sodium hydroxide with the balance water. Over the course of about 137 hours on stream, conversion of glycerol ranged from about 75% to 77% and selectivity to propylene glycol was about 92% to 93%. This represented expected selectivity for this catalyst, but slightly lower than normal conversion. Specifically, following equilibration of the catalyst over 137 hours, the conversion of glycerol reached 77% and the carbon molar selectivity to propylene glycol was 93%. Selectivity for the larger byproducts was as follows: 3.5% to ethylene glycol, 2.3% to sodium lactate, 0.4% to methanol, 0.2% to ethanol, and 0.5% to propanols.) Results from this baseline test are shown in Table 1.

TABLE 1

Baseline of Catalyst Before Testing Simulated Recycle

|  | F167-1 | F167-2 | F167-3 | F167-3 |
|---|---|---|---|---|
| System Conditions |  |  |  |  |
| Total hours on stream | 16:35:00 | 42:39:00 | 65:25:00 | 137:03:00 |
| Cat. Bed Temp (° C.) | 190 | 190 | 190 | 190 |
| System Pressure | 1200 | 1200 | 1200 | 1200 |
| Liq. Feed Rate (ml/hr) | 35 | 35 | 35 | 35 |
| Glycerol Feed Conc. (wt %) | 40.56 | 40.56 | 40.56 | 40.56 |
| % Wt. Recovery | 98.38 | 97.25 | 97.62 | 98.31 |
| % Carbon Recovery | 96.94 | 100.76 | 98.10 | 95.96 |
| Glycerol Conv.(By Difference) | 0.75 | 0.75 | 0.76 | 0.77 |
| Selectivities (carbon, based on total products) |  |  |  |  |
| PG C Molar Selectivity | 0.92 | 0.92 | 0.93 | 0.93 |
| EG C Molar Selectivity | 0.035 | 0.035 | 0.035 | 0.035 |
| Lactate C Molar Selectivity | 0.025 | 0.024 | 0.023 | 0.023 |
| Glycerate C Molar Selectivity | 0.0061 | 0.0046 | 0.0041 | 0.0032 |
| Glycolate C Molar Selectivity | 0.0011 | 0.0010 | 0.0009 | 0.0009 |
| Formate C Molar Selectivity | 0.0007 | 0.0035 | 0.0006 | 0.0012 |
| Methanol C Molar Selectivity | 0.002 | 0.004 | 0.003 | 0.004 |
| Ethanol C Molar Selectivity | 0.000 | 0.001 | 0.002 | 0.003 |
| 1-Propanol C Molar Selectivity | 0.005 | 0.003 | 0.002 | 0.003 |
| 2-Propanol C Molar Selectivity | 0.002 | 0.002 | 0.001 | 0.002 |

The catalyst was then used to test feeds that use propylene glycol as the primary solvent for glycerol instead of water. The first reactor feed substituted propylene glycol for the water solvent and was used in test runs F169-1 through F169-3. The second and third feeds comprised a mixture having a water balance more similar to the feed generated from the recycled product stream. These feeds take into account the amount of water recycled with the propylene glycol and generated from the dehydroyxlation reaction. These feeds were used in test runs F169-4 through F169-6, and test runs F169-7 through F169-10, respectively. The compositions are shown in Table 2. (Note that since this was a proof of principle testing none of the feeds contained ethylene glycol or other byproducts that are produced in the expected side reactions.)

TABLE 2

PG Solvent Feeds Used In F169 Test Runs

| By wt % | Feed 1 | Feed 2 | Feed 3 |
|---|---|---|---|
| Glycerol | 39.6% | 39.4% | 39.1% |
| Propylene Glycol | 58.2% | 46.5% | 45.2% |
| Water | 1.2% | 13.1% | 14.7% |
| NaOH | 1.0% | 1.0% | 1.0% |
| Tests Used | 1-3 | 5-6 | 7-10 |

The results from the tests are shown below in Table 3, along with the baseline result from F167-4 (see Table 1).

TABLE 3

Simulated Product Recycled as Solvent Tests

| Conditions | F167-4 | F169-1 | F169-2 | F169-3 | F169-5 | F169-6 | F169-7 | F169-8 | F169-9 | F169-10 |
|---|---|---|---|---|---|---|---|---|---|---|
| Total hours on stream | 137:03:00 | 168:52:00 | 192:19:00 | 215:34:00 | 306:40:00 | 352:12:00 | 376:47:00 | 471:53:00 | 551:47:00 | 640:35:00 |
| Cat. Bed Temp (° C.) | 190 | 190 | 190 | 180 | 180 | 180 | 180 | 170 | 170 | 170 |
| System Pressure | 1200 | 1200 | 1200 | 1200 | 1200 | 1400 | 1000 | 1200 | 1200 | 1200 |
| Liq. Feed Rate (ml/hr) | 35 | 35 | 35 | 35 | 35 | 35 | 35 | 35 | 25 | 25 |
| Glycerol Feed Conc. (wt %) | 40.56 | 39.62 | 39.62 | 39.62 | 39.44 | 39.44 | 39.06 | 39.06 | 39.06 | 39.06 |
| Feed Solvent | Water | PG1 | PG1 | PG1 | PG2 | PG2 | PG3 | PG3 | PG3 | PG3 |
| % Wt. Recovery | 98.31 | 98.38 | 98.24 | 98.71 | 98.48 | 98.17 | 98.56 | 97.75 | 98.42 | 97.62 |
| % Carbon Recovery | 95.96 | 100.29 | 98.47 | 97.92 | 95.83 | 95.96 | 97.56 | 97.12 | 97.77 | 99.07 |
| Glycerol Conv. (By Difference) | 0.77 | 0.87 | 0.83 | 0.72 | 0.61 | 0.60 | 0.58 | 0.48 | 0.51 | 0.51 |
| Selectivities (carbon, based on total products) | | | | | | | | | | |
| PG C Molar Selectivity | 0.93 | 0.73 | 0.78 | 0.85 | 0.81 | 0.81 | 0.80 | 0.88 | 0.75 | 0.71 |
| EG C Molar Selectivity | 0.035 | 0.047 | 0.042 | 0.032 | 0.031 | 0.030 | 0.028 | 0.027 | 0.026 | 0.024 |
| Lactate C Molar Selectivity | 0.023 | 0.024 | 0.027 | 0.022 | 0.042 | 0.041 | 0.050 | 0.043 | 0.042 | 0.044 |
| Glycerate C Molar Selectivity | 0.0032 | 0.0004 | 0.0004 | 0.0000 | 0.0000 | 0.0000 | 0.0004 | 0.0005 | 0.0004 | 0.0005 |
| Glycolate C Molar Selectivity | 0.0009 | 0.0000 | 0.0000 | 0.0000 | 0.0000 | 0.0000 | 0.0000 | 0.0000 | 0.0000 | 0.0000 |
| Formate C Molar Selectivity | 0.0012 | 0.0078 | 0.0093 | 0.0117 | 0.0203 | 0.0214 | 0.0219 | 0.0000 | 0.0304 | 0.0318 |
| Methanol C Molar Selectivity | 0.004 | 0.000 | 0.000 | 0.000 | 0.000 | 0.000 | 0.000 | 0.000 | 0.000 | 0.000 |
| Ethanol C Molar Selectivity | 0.003 | 0.041 | 0.038 | 0.034 | 0.027 | 0.023 | 0.034 | 0.023 | 0.027 | 0.028 |
| 1-Propanol C Molar Selectivity | 0.003 | 0.004 | 0.003 | 0.002 | 0.000 | 0.001 | 0.001 | 0.000 | 0.000 | 0.000 |
| 2-Propanol C Molar Selectivity | 0.002 | 0.016 | 0.018 | 0.015 | 0.024 | 0.024 | 0.028 | 0.018 | 0.024 | 0.022 |

In tests 1 through 3, a feedstock was processed that was prepared using propylene glycol as the solvent instead of water. Performance of the catalyst initially increased glycerol conversion from about 77% to about 87%, but declined in propylene glycol selectivity from about 93% down to about 73%. For test run F169-2, the catalyst presumably equilibrated over the next 24 hours as conversion of glycerol fell below the baseline to about 83%, but propylene glycol selectivity was still quite low at about 78%.

For run F169-3, the temperature was dropped from 190° C. down to 180° C., which resulted in a final glycerol conversion of about 72% and selectivity to propylene glycol of about 85%. This compared favorably to the baseline water solvent test. Specifically, the glycerol conversion was only about 5 percentage points lower than the baseline, and only about 8 percentage points behind in propylene glycol selectivity. However, overall byproduct production went up including higher selectivity to ethanol, formate, and propanol, while ethylene glycol selectivity eventually settled slightly below the baseline.

In the second round of tests, two feeds were used that more closely resembled the water content expected in a feed prepared from a steady-state recycled product. However, for run F169-5, running the feed with water and propylene glycol as the solvent, after it was allowed to equilibrate for 90 hours, resulted in a drop in glycerol conversion down to about 61% along with a reduction in propylene glycol selectivity to about 81%.

To determine the impact of hydrogen availability on the performance, the next two samples were taken after equilibrating to higher and lower hydrogen pressures in the reactor while maintaining the same 5:1 molar ratio excess of hydrogen as the baseline, as test runs F169-6 and F169-7 illustrate, respectively. This had no affect on the performance of the catalyst keeping a constant glycerol conversion of about 60%, and propylene glycol selectivity of about 80%.

For test run F169-8, the temperature was dropped to about 170° C. from about 180° C., which resulted in a drop in glycerol conversion to about 48%, However, the selectivity was high or at about 88%, which was the highest that had been observed using any amount of propylene glycol as the solvent. The higher than baseline side products consisted mainly of lactate, formate, ethanol, and propanol. Again, ethylene glycol selectivity was lower than baseline, but not enough to have a major impact on downstream separations.

For test runs F169-9 and F169-10, the flow rate of feed was dropped to about 25 ml/hr. This resulted in a negligible glycerol conversion increase and an eventual drop in propylene glycol selectivity down to about 71%. It should be noted that a flow rate of about 25 ml/hr has historically been difficult for a 30 cc reactor to maintain consistent results due to expected channeling at such low flow rates. This is most likely exacerbated by the use of a higher viscosity feed.

Given the results from test run F169-8, where the temperature of the reactor was at 170° C. down from the baseline case of 190° C., the propylene glycol selectivity was 88% versus the baseline of 93%. It is anticipated that this could be further improved by one of skill in the art with some process tuning. However, the glycerol conversion drop from the baseline of 76% down to 48% represents a significant change. As such, the reactor bed would have to be much larger, incurring equipment and catalyst costs, but this would need to be compared against the impact on the downstream separations given that the amount of water sent to separations is greatly reduced by nearly an order of magnitude.

It should be appreciated that the disclosed processes and systems could be optimized with respect to the baseline by one of skill in the art by varying the process parameters and/or by using better performing catalysts. For instance, the process can be carried out at temperatures from about 160° C. to about 240° C., and at pressures from about 400 psi to about 1600 psi. Catalysts disclosed in U.S. Pat. No. 6,841,085, and co-pending U.S. patent application Ser. No. 12/711,020, entitled, "Catalysts And Processes For The Hydrogenolysis Of Glycerol And Other Organic Compounds For Producing Polyols And Propylene Glycol," filed on Feb. 23, 2010, and incorporated herein by reference, are believed to be suitable for the process and system disclosed herein.

The product recycle processes and systems disclosed herein will reduce energy and resource requirements and costs by eliminating the addition and removal of water solvent as a result of the recycling of hot reactor effluent into the glycerol feed, while at the same time not significantly impacting the amount of propylene glycol produced.

Additionally, other aqueous catalytic processes could also benefit from the disclosed processes and systems, particularly technologies that produce a solvent as a product and require a more dilute feed.

In view of the many possible embodiments to which the principles of the disclosed processes and systems may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A process for producing propylene glycol, comprising:
   combining a solvent comprising propylene glycol with a feed comprising glycerol to provide a diluted glycerol feed;
   reacting said diluted glycerol feed with a catalyst in the presence of a soluble base to convert the glycerol to a product comprising propylene glycol;
   recycling back into the process at least a portion of propylene glycol product as a solvent for the glycerol feed; and
   wherein at least a portion of the soluble base is also recycled back into the process along with at least a portion of the product comprising propylene glycol as a solvent for the glycerol feed.

2. The process of claim 1 wherein the soluble base is sodium hydroxide.

3. The process of claim 1 wherein the diluted glycerol feed comprises about 1% by weight soluble base.

4. The process of claim 1 wherein the base is sodium hydroxide.

5. The process of claim 1 wherein from up to about 60% of the product is recycled back.

6. The process of claim 1 wherein the diluted glycerol feed comprises from about 40% to 60% by weight glycerol.

7. The process of claim 1 wherein the diluted glycerol feed comprises from about 40% to 60% by weight propylene glycol.

8. The process of claim 1 wherein reacting said diluted glycerol feed with a catalyst results in about 70% or greater selectivity to propylene glycol.

9. The process of claim 1 wherein the diluted glycerol feed comprises less than about 12% water by weight.

* * * * *